Aug. 20, 1946. H. C. SWIM Plant Pat. 709
ROSE PLANT
Filed Feb. 6, 1945
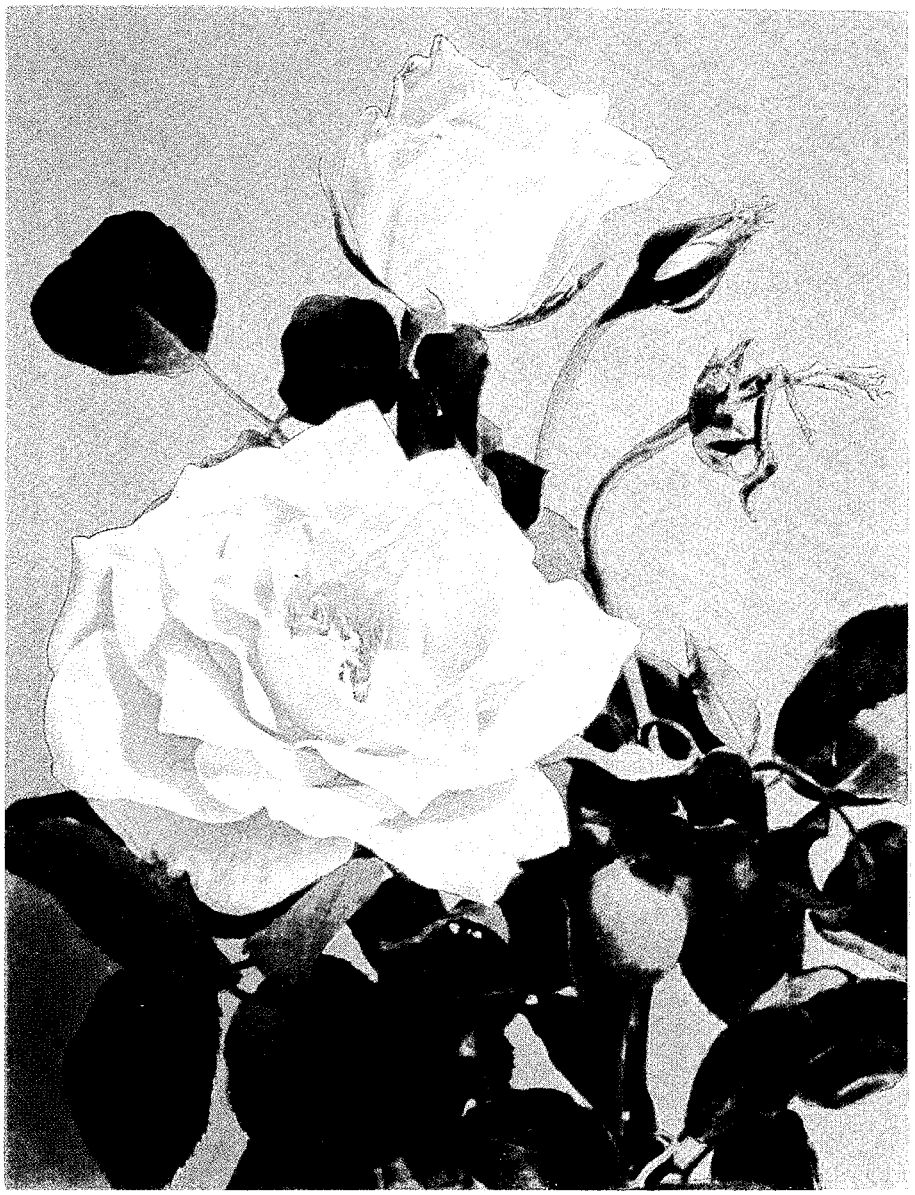
Inventor
H. C. Swim
By Robb & Robb
His Attorneys Patented Aug. 20, 1946

Plant Pat. 709

UNITED STATES PATENT OFFICE

709

ROSE PLANT

Herbert C. Swim, Ontario, Calif., assignor to Armstrong Nurseries, Inc., Ontario, Calif., a corporation of California Application February 6, 1945, Serial No. 576,485

1 Claim. (Cl. 47—61)

The present invention relates to a new and distinct variety of rose plant resulting from a cross of two well-known varieties and constituting desirable improvement in the characteristics of one of its parents.

While the flower of this new variety is similar to the seed parent in shape and color, it is substantially larger in both bud and open flower, a desirable advantage in the use of the plant both for cut flowers or garden decoration purposes.

By way of further distinction from its parent "Picture," the flower has from ten to fifteen fewer petals and a very slightly deeper shade of color, and the plant is more vigorous and more upright than this parent variety, with longer, more slender individual flower stems.

It is also notable that the foliage is somewhat more sparse than "Picture" and has leaves that are slightly longer and leaflets slightly smaller, but to its betterment the foliage is more resistant to mildew.

Fragrance is somewhat more pronounced in this variety than in either of its parents, both of which are relatively scentless. It will thus be apparent that by this cross, many of the desirable characteristics of the pollen parent have been transmitted to this new variety, resulting in the elimination of or improvement in some of the faulty traits found in the less desirable parent variety.

Asexual reproduction of this new variety shows the foregoing characteristics come true to form and are established.

The drawing shows specimens of this variety in various stages of development.

The following is a detailed description of this new variety, the color terminology being in accord with the Robert F. Wilson Horticultural Colour Chart, except where otherwise designated as taken from Ridgway's Color Standard:

Type: Bush; for cut flowers and garden decoration.

Class: Hybrid tea.

Breeding: Seedling.

*Seed parent.*—"Picture."

*Pollen parent.*—"Charlotte Armstrong" (Pl. Pat. No. 455).

Propagation: Holds its distinguishing characteristics through succeeding propagations by budding, which is the only method tried up to the present.

*Flower*

Locality where grown: Ontario, California.

Flowers borne: Singly to stem; on strong, medium-long stems.

Quantity of bloom: Moderate; outdoors.

Continuity: Intermittent.

Fragrance: Moderate; tea.

Bud:

*Peduncle.*—Medium length; medium heavy; erect; almost smooth; few gland-tipped cilia, hairs.

*Color.*—Near Biscay Green, Plate XVII (Ridgway).

*Before calyx breaks.*—Size—small to medium. *Form*—ovoid, without a conspicuous neck; with foliaceous appendages, tomentum, gland-tipped cilia, glandular bloom, on the surface of the bud; with slender, much-cut foliaceous parts extending beyond the tip of the bud equal to ¼ or more of its length.

*As calyx breaks.*—*Color*—base color near Rose Opal, Plate 022/1, shaded and striped with near Rose Opal, Plate 022. *Inner surface*—usually two sepals with stipitate glands only. Three sepals with stipitate glands and woolly tomentum.

*As first petal opens.*—*Size*—medium. *Form*—Ovoid to globular. *Color*—outside—near Rose Opal, Plate 022/1, shaded and striped with near Rose Opal, Plate 022, changing toward base to near Begonia, Plate 619/1. Small area at base near Mimosa Yellow, Plate 602/1. Inside—near Rose Opal, Plate 022/1, shaded and striped with near Rose Opal, Plate 022, changing toward base to near Begonia, Plate 619/1. Small area at base near Mimosa Yellow, Plate 602/1. *Opening*—Opens up well.

Bloom:

*Size.*—When fully open—medium to large; four inches to five inches.

*Petalage.*—Double (but stamens not hidden); from 23 to 27 petals; arranged irregularly; usually has five to eight petaloids.

*Form.*—Full, high center at first: becoming cupped; petals remaining at first very tightly cupped but tips rolled outward; becoming later, at maturity, loosely cupped but tips rolled outward.

Petals: Moderately thick; with inside satiny and outside satiny-velvety.

*Shape.*—Outside—round, mucronate; scalloped with apex flat, with one notch. Intermediate—obovate, mucronate; scalloped with apex flat, with one notch sometimes, but usually none. Inside—obovate, mucronate; scalloped with apex flat, with one notch sometimes but usually none.

*Color.*—Colors may be modified by being shaded or washed with other colors.

This description of a newly opened flower was made from a rose grown outdoors in the month of October, 1944, at Ontario, California:

*Color.*—*Outside petal*—outside surface: near Rose Opal, Plate 022/2, with veining of near Rose Opal, Plate 022/1, gradually changing toward the base to near Begonia, Plate 619/1, with small area at base near Mimosa Yellow, Plate 602/1; Inside surface: same as given above for outside surface but with less veining. *Intermediate petal*—outside surface: near Rose Opal, Plate 022/1, changing toward base to near Sulphur Yellow, Plate 1/2; inside surface: same as given above for outside surface of intermediate petal. *Inner petal*—outside surface: same as given above for outside surface of intermediate petal, but showing a thin white line running from near base to near apex on some petals; inside surface: same as given above for inside surface of intermediate petal.

This description was made from a rose that was open for three days indoors in October, 1944, at Ontario, California:

*Color.*—*Outside petal*—outside surface: near Rose Opal, Plate 022/3, with veining of near Rose Opal, Plate 022/2; inside surface: same as given above for outside surface but with less veining. *Inside petal*—outside surface: same as given above for outside surface of outside petal; inside surface: same as given above for inside surface of outside petal.

*General color Effect.*—Newly opened flower—Rose Opal, Plate 022/2. Three days open—Rose Opal, Plate 022/3.

*Behavior.*—Drop off cleanly. Fades more rapidly in extremely hot weather.

*Flower longevity.*—On bush in garden—2 to 3 days in October. Cut roses grown outdoors kept at living room temperatures—3 to 4 days in October.

*Reproductive organs*

Stamens: Many; arranged irregularly, partly, about pistils, mixed with petaloids.

Filaments: Medium length; most with anthers.

Anthers: Medium size; open at various times.

*Color.*—Near Cinnamon Buff, Plate XXIX (Ridgway).

Pollen: Moderately abundant.

*Color.*—Near Cinnamon Buff, Plate XXIX (Ridgway).

Pistils: Medium number.

Styles: Uneven; medium length; medium heavy; bunched.

Stigma: White or near white.

Ovaries: Enclosed in, some protruding from, calyx.

Hips: Short; globular with inconspicuous neck; moderately smooth; glandular; walls thick, fleshy.

*Color.*—Near Absinthe Green, Plate XXXI (Ridgway).

Sepals: Permanent; moderately short; spear-shaped.

*Color.*—Inside—near Mytho Green, Plate XLI (Ridgway). Outside—near Light Cress Green, Plate XXXI (Ridgway).

Seeds: Few; medium size.

*Plant*

Foliage:

*Leaves.*—Compound of 5 to 7 leaflets; normally abundant; moderately large; moderately heavy, leathery, semi-glossy.

*Leaflets.*—Ovoid with apex acute; base round; margin irregularly serrate.

*Color.*—*Mature*—upper surface—near Empire Green, Plate XXXII (Ridgway); under surface—near Light Elm Green, Plate XVII (Ridgway). Rib and margins near Vinaceous Drab, Plate XLV (Ridgway). *Young*—upper surface—near Yellowish Olive, Plate XXX (Ridgway); under surface—near Vinaceous Drab, Plate XLV (Ridgway).

*Rachis.*—Medium heavy. Upper side—grooved; glandular. Under side—moderately smooth to hairy, prickly.

*Stipules.*—Medium length; medium width; with moderately short points, turning out at an angle of less than 45°.

*Disease.*—Resistant to mildew.

Growth:

*Habit.*—Bushy; upright.

*Growth.*—Vigorous.

*Canes.*—Medium heavy.

*Main stems.*—*Color*—near Deep Dull Yellow Green (1), Plate XXXII (Ridgway). *Large prickles*—several; medium long; hooked downward; with narrow to broad base. Color—near Roods Brown, Plate XXVIII (Ridgway). *Small prickles*—few. Color—near Roods Brown, Plate XXVIII (Ridgway). *Hairs*—none.

*Branches.*—Near Chromium Green, Plate XXXII (Ridgway). *Large prickles*—several; medium long; straight; with narrow to broad base. Color—near Roods Brown, Plate XXVIII (Ridgway). *Small prickles*—few. Color—near Roods Brown, Plate XXVIII (Ridgway). *Hairs*—none.

*New shoots.*—Near Clear Fluorite Green, Plate XXXII (Ridgway). Side exposed to sun near Vinaceous Drab, Plate XLV (Ridgway). *Large prickles*—several; medium long; hooked downward; with long, narrow base. Color—near Deep Purplish Vinaceous, Plate XLIV (Ridgway). *Small prickles*—few. Color—near Deep Purplish Vinaceous, Plate XLIV (Ridgway). *Hairs*—none.

I claim:

A new and distinct variety of hybrid tea rose plant, characterized as to novelty by the increase in size of the bud and open flower over that of its seed parent; increase in vigor and uprightness of the plant over said parent, combined with longer and more slender individual flower stems and higher degree of resistance of the foliage to mildew; and by somewhat more pronounced fragrance than that of either of its parents, substantially as shown and described.

HERBERT C. SWIM.